(12) United States Patent
Roppelt

(10) Patent No.: US 7,882,724 B2
(45) Date of Patent: Feb. 8, 2011

(54) METHOD AND CONFIGURATION FOR TESTING A PARTICLE FILTER FOR AN INTERNAL COMBUSTION ENGINE

(76) Inventor: Helmut Roppelt, Breslauer Strasse 10, 76139 Karlsruhe (DE)

(*) Notice: Subject to any disclaimer, the term of this patent is extended or adjusted under 35 U.S.C. 154(b) by 5 days.

(21) Appl. No.: 12/344,720

(22) Filed: Dec. 29, 2008

(65) Prior Publication Data

US 2009/0158814 A1 Jun. 25, 2009

Related U.S. Application Data

(63) Continuation of application No. PCT/EP2007/005569, filed on Jun. 25, 2007.

(30) Foreign Application Priority Data

Jun. 27, 2006 (DE) .................. 10 2006 029 493

(51) Int. Cl.
*G01N 7/00* (2006.01)
(52) U.S. Cl. .................................... 73/23.31
(58) Field of Classification Search ............... 73/23.31
See application file for complete search history.

(56) References Cited

U.S. PATENT DOCUMENTS

| | | | |
|---|---|---|---|
| 5,110,747 A * | 5/1992 | Pataschnick et al. ....... | 73/23.31 |
| 7,075,019 B2 | 7/2006 | Bergman et al. | |
| 7,351,273 B2 * | 4/2008 | Handte ........................... | 95/1 |
| 7,412,335 B2 | 8/2008 | Anderson et al. | |

FOREIGN PATENT DOCUMENTS

| | | |
|---|---|---|
| DE | 196 17 160 C1 | 7/1997 |
| EP | 0 632 255 A1 | 1/1995 |
| WO | 02/102663 A1 | 12/2002 |
| WO | 2006/020731 A1 | 2/2006 |

OTHER PUBLICATIONS

International Search Report, dated Dec. 20, 2007.
Verein Deutscher Ingenieure: "VDI 3926 Testing of cleanable filter media—Standard test for the evaluation of cleanable filter media", VDI/DIN-Handbuch Reinhaltung der Luft, vol. 6, Oct. 2004, pp. 1-31, XP00810556.
Filteq GmbH Karlsruhe: "Filter test rig accoding to VDI/DIN 3926 and ASTM D 6830-02" Sep. 2004, Internet, www.filteq.de/Filter_tester_heater_Nov_2004.pdf, XP007910410.

(Continued)

*Primary Examiner*—Hezron Williams
*Assistant Examiner*—Alex Devito
(74) *Attorney, Agent, or Firm*—Laurence A. Greenberg; Werner H. Stemer; Ralph E. Locher

(57) ABSTRACT

A particle filter for an internal combustion engine, in particular a soot particle filter, can be tested. The filter is subjected at the inlet side to a hot gas flow which is laden with particles. The particles are supplied to the hot gas flow from a particle storage container by means of a dosing device. The quantity of particles which is introduced into the hot gas flow during a predefined measurement time period is determined by weighing the particle storage container. There is also provided a configuration for carrying out the method.

10 Claims, 1 Drawing Sheet

OTHER PUBLICATIONS

Filteq GmbH Karlsruhe: "Der Staubdosierer NDF 100, Version NDF 100-3FI (Injektor Dispergierkopf)" Auszug aus Bedienungsanleitung, Jan. 2005, Internet, http://www.filteq.de/Staubdosier_BDF 100-3FI_-_Injektor_-_Auszug.pdf, XP007910409.

* cited by examiner

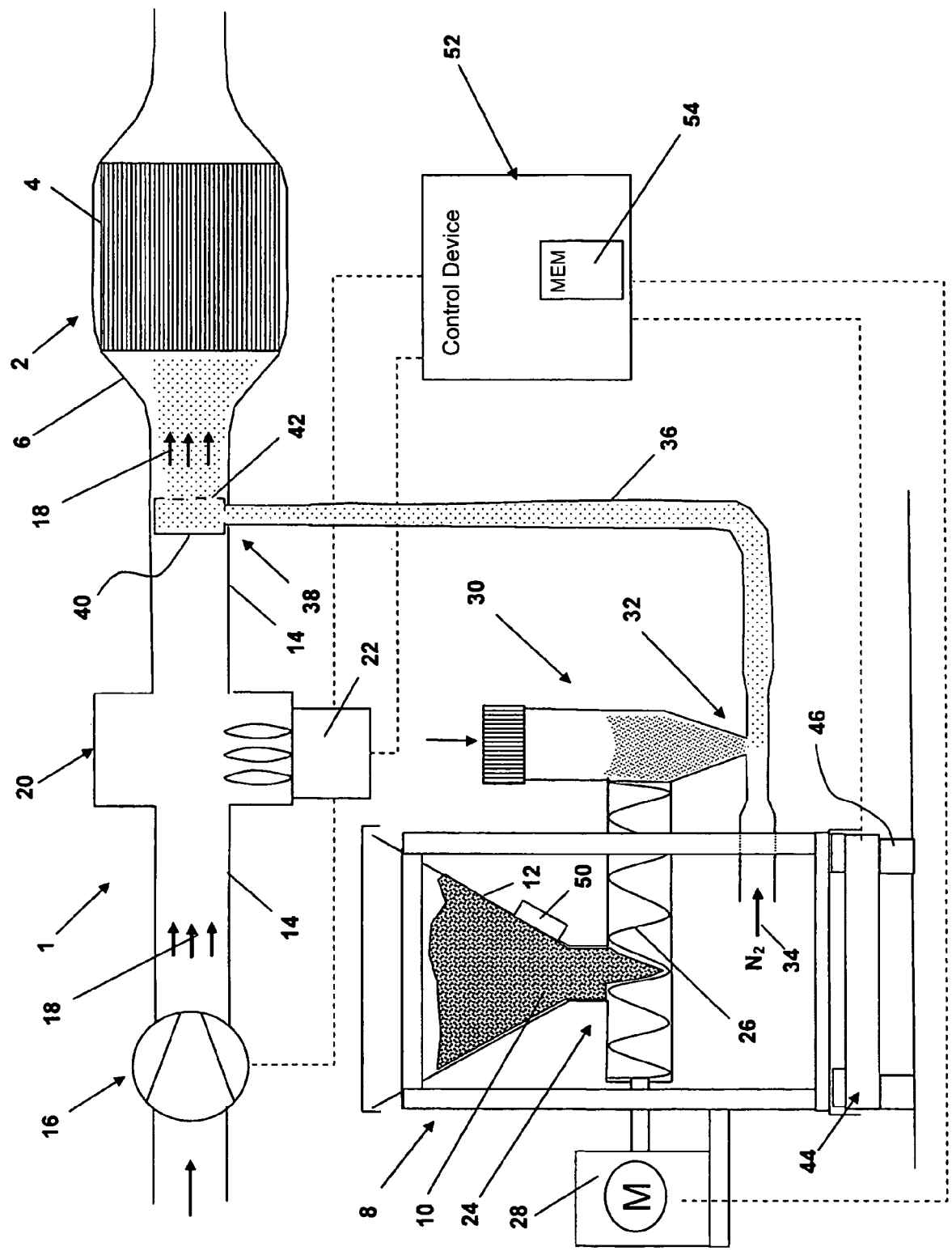

METHOD AND CONFIGURATION FOR TESTING A PARTICLE FILTER FOR AN INTERNAL COMBUSTION ENGINE

CROSS-REFERENCE TO RELATED APPLICATION

This is a continuation, under 35 U.S.C. §120, of copending international application No. PCT/EP2007/005569, filed Jun. 25, 2007, which designated the United States; this application also claims the priority, under 35 U.S.C. §119, of German patent application No. 10 2006 029 493.9, filed Jun. 27, 2006; the prior applications are herewith incorporated by reference in their entirety.

BACKGROUND OF THE INVENTION

Field of the Invention

The invention relates to a method and to an configuration for testing a particle filter for an internal combustion engine, in particular a soot particle filter, which is subjected at the inlet side to a hot gas flow laden with particles.

In the particle filters which are used nowadays in motor vehicles, in particular in the legally stipulated soot particle filters in the exhaust systems of diesel engines for reducing the fine dust content in the ambient air, there is the problem that the actual filter insert must be inserted into a housing which is adapted to the structural conditions of the motor vehicle with regard to the profile of the exhaust-line system.

Here, there is the problem that, as a result of the shape of the filter housing, turbulence can be generated in the exhaust gas, which turbulence leads to locally increased concentrations of particles in the filter substrate, whereas virtually no particles are accumulated at other points of the filter substrate. As a result of the different particle concentrations, there is the risk that, during the regeneration of the filter, soot clusters are formed which locally generate an excessive temperature increase. As a result it is possible for the filter substrate to become damaged after only a few regeneration cycles.

To counteract the above-stated problems, the filters, that is to say the filter housings and the substrates which are contained therein, are subjected in a known way to endurance testing, in which the filter is usually, in known testing configurations, laden with particles over a relatively long time period by means of an internal combustion engine, and subsequently regenerated at predefined time intervals on the basis of different driving states.

Here, there is the difficulty that even the exhaust gas generated by a diesel engine has, at 5 to 20 mg per cubic centimeter, only a comparatively low concentration of particles, such that for the complete loading of an average passenger motor vehicle filter with a quantity of, for example, 20 to 50 mg, a time duration of approximately 10 hours is necessary, which makes endurance testing of the filter in all of the driving states which are to be simulated very time-consuming.

A further problem of the above-stated test beds is that, to determine the quantity of particles contained in the filter, the latter must generally be dismounted, weighed manually on a suitable set of precision scales, and subsequently re-installed in the testing configuration, which additionally increases the time expenditure and furthermore also increases the risk of systematic errors in the endurance testing of the particle filters.

The above-mentioned problems are aggravated yet further in particle filters for other engine types, for two-stroke and four-stroke spark-ignition engines, on account of the reduced quantity of particles in the exhaust gas in relation to diesel engines.

SUMMARY OF THE INVENTION

It is accordingly an object of the invention to provide a method an a configuration for testing a particle filter for an internal combustion engine which overcomes the above-mentioned disadvantages of the heretofore-known devices and methods of this general type and which allows shortening the time duration required for testing the particle filters.

With the foregoing and other objects in view there is provided, in accordance with the invention, a method for testing a particle filter for an internal combustion engine, such as a soot particle filter. The method comprises:

subjecting the filter, at an inlet side thereof, to a hot gas flow laden with particles;

supplying the particles to the hot gas flow from a particle storage container by way of a dosing device; and determining a quantity of particles being introduced into the hot gas flow during a predefined measurement time period by weighing the particle storage container.

With the above and other objects in view there is also provided, in accordance with the invention, a configuration for testing a particle filter for an internal combustion engine, comprising:

means for subjecting an inlet side of the particle filter to a hot gas flow laden with particles;

a particle storage container containing particles to be supplied into the hot gas flow;

a dosing device configured to extract the particles from the particle storage container and supplying the particles in a predefined quantity per unit time to the hot gas flow; and a weighing device configured to weigh said particle storage container, for determining a total weight of the particle storage container with the particles contained therein.

In other words, according to the invention, in a method for testing a particle filter for an internal combustion engine, which particle filter comprises a housing with a filter substrate contained therein and which particle filter is subjected at the inlet side to a hot gas flow which is laden with particles, in particular with exhaust gas, the particles are stored in a particle storage container. During a test run, the particles are extracted from said container by means of a dosing device and are introduced, preferably in fluid form, into the hot gas flow. Here, in order to determine the quantity of particles which is introduced during a predefined measurement time period, according to the invention, the entire particle storage container with the particles contained therein is weighed, such that it is possible, in particular by calculating the difference between the initial weight of the storage container and the weight of the storage container after a predefined time duration, to calculate the total quantity of the particles extracted from the storage container, which total quantity corresponds to the quantity of particles introduced into the hot gas flow.

The invention is also advantageous since, as a result of the external storage of particles in the particle storage container—which particles, in the case of diesel engines, are preferably provided in the form of purchasable industrial soot—it is possible to obtain a considerably higher concentration of soot particles in the hot gas flow, which concentration lies in the region of 1000 mg per cubic meter. In this way, it is possible to reduce the time duration for the complete loading of the filter even in relation to old diesel engines which are operated in the excessively rich range with an excessive injection quantity of diesel fuel, to approximately $\frac{1}{50}^{th}$ to $\frac{1}{100}^{th}$ of the time required using the engines.

A further advantage of the method according to the invention is that, for endurance testing, a time-consuming dismounting and re-installation of the particle filter out of and into the testing configuration, which is often associated with systematic errors, in order to weigh said particle filter is no longer strictly necessary, such that in addition to a further time saving, the risk of systematic errors in the weighing process is also reduced.

A further substantial advantage of the method according to the invention is, in this connection, that the total weight of the particle storage container is determined over the entire testing time period at predefined time intervals of, for example, one second, and it is thereby advantageously possible, by calculating the difference between the instantaneous total weight and the initial total weight of the particle storage container, to carry out an online measurement of the total quantity of particles which has been extracted from the particle storage container, as a result of which the total quantity of the particles supplied to the particle filter—and therefore the degree of loading—can be followed with a high degree of precision over the entire loading cycle.

As a result of said online measurement at predefined time intervals, it is also possible, in particular when using a dosing device with a variable delivery capacity, that is to say a variable quantity of particles delivered per unit time, for the delivery capacity to be correspondingly increased or reduced in order to match the total quantity of delivered particles at the end of the measurement time period to a desired default value or nominal value.

Here, it may also advantageously be provided that the delivery capacity of the dosing device is increased or reduced by a fixed value, for example by a fixed percentage of the maximum delivery capacity, and that, for example after three seconds, a running mean value is formed from the last, for example, three measurements of the extracted particle quantity, which running mean value forms an actual value for the extracted total quantity of particles, which actual value is subsequently compared with a nominal value for the extracted total quantity of particles, said nominal value being determined by calculation on the basis of the time duration which has elapsed since the beginning of the testing time period and the respective associated delivery capacity of the dosing device.

According to a further concept on which the invention is based, the delivery capacity of the dosing device is increased preferably by a fixed value and for a fixed time period, for example three seconds or three measurement intervals, if the actual value falls below the nominal value for the extracted total quantity of particles, and said delivery capacity is correspondingly reduced in the event of the actual value exceeding the nominal value.

This type of increase and reduction of the delivery capacity of the dosing pump by a fixed value, which correspondingly lies above or below the average value for the delivery capacity required for calculating the nominal value or target value, provides the advantage that the regulation problems which conventionally occur in the case of relatively sensitive regulation, such as overdriving of the regulator or else underdriving of the same, do not occur in practice even if the particle quantity which is delivered by the dosing device is briefly sharply increased or else sharply reduced.

A brief increase or reduction of said type is generated in particular when a knocking and/or shaking device is provided on the particle storage container, which knocking and/or shaking device imparts small shocks to the storage container at regular time intervals in order to prevent the formation of lumps or particle bridges which then pass, in particular in the form of lumps, into the working region of the dosing device and which briefly sharply increase the delivery quantity —and therefore the delivery capacity.

In the preferred embodiment of the invention, the particles are preferably delivered by means of a dosing worm or delivery worm which is preferably arranged directly below the particle storage container, for which purpose the worm is driven at a predefined rotational speed by an electric motor and a corresponding rotational speed regulator.

In order to, for example, increase the delivery quantity of particles in the above-described manner, the rotational speed of the motor is increased, or reduced, by a predefined rotational speed value if the actual value for the delivered total quantity, which is determined as a running mean value by weighing the particle storage container, exceeds, or falls below, the default value or nominal value.

According to a further concept on which the invention is based, the particles, after emerging out of the feed worm, are passed for example by means of a known venturi nozzle into a fluid which preferably comprises an inert carrier gas such as nitrogen. The fluid is fed via a supply line, for example a hose, to an injector which is arranged upstream of the inlet of the particle filter. The injector may for example comprise a tube which protrudes directly into the hot gas flow and which has holes formed therein on the downstream side, out of which holes the fluid emerges, said fluid being delivered directly to the inlet of the particle filter after being mixed with the hot gas.

In the preferred embodiment of the invention, the hot gas flow is heated by means of a burner, for example an oil burner, with a compressor or at least one fan being arranged preferably upstream of the burner with regard to a typical configuration of the hot gas flow for an internal combustion engine, which compressor or fan inducts the air for generating the hot gas flow and pre-compresses said air to a pressure of 0.2 to 1.5 bar before said air is heated by the burner.

Although the testing configuration according to the invention and the method according to the invention can also be used with a conventional internal combustion engine for generating the hot gas flow, the use of a burner provides the advantage that only the energy for heating the hot gas, that is to say the air inducted by the compressor, for example a rotary piston compressor, need be provided, with it also being possible for the temperature of the hot gas flow to be regulated with a considerably greater degree of precision. Furthermore, the infrastructure required for operating an engine, such as a cooling device, braking device for dissipating the generated mechanical power, and also the sound deadening etc., may be dispensed with, and the magnitude of the admission pressure of the hot gas can be increased or reduced, with a comparatively reduced level of device expenditure, in a defined, reproducible manner by operating the compressor in a corresponding manner to an internal combustion engine.

It is thus possible, for example, for the pressure of the hot gas flow to be increased not only to approximately 1 bar—as in modern-day internal combustion engines—but rather also to 2 bar or even 3 bar by increasing the number of upstream compressors, as a result of which it is also possible to test particle filters which will be used in future internal combustion engine with turbochargers in which the charge pressure is for example two bar or more, and in which the pressure in the exhaust system is correspondingly also increased by approximately the same value.

Other features which are considered as characteristic for the invention are set forth in the appended claims.

Although the invention is illustrated and described herein as embodied in method and device for testing a particle filter for an internal combustion engine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWING

The FIGURE is a schematic illustration of a testing configuration according to the invention, illustrating the mode of operation of the individual components.

DETAILED DESCRIPTION OF THE INVENTION

Referring now to the sole FIGURE of the drawing in detail, the configuration according to the invention comprises a test bed 1 for testing a particle filter 2 for an internal combustion engine. The particle filter 2 has a filter substrate 4 which is held in a filter housing 6. A particle storage container 8 stores particles 10 in a relatively large quantity. In the event that a soot filter 2 for a diesel engine is to be tested, it is possible, for example, for 8 kg of industrial soot to be held in the housing 12, which preferably tapers downward in the shape of a funnel, of the storage container 8, in order to simulate for example an endurance test of the filter 2 over three to four days under different driving states of a motor vehicle.

Here, a hot gas flow 18 is supplied to the particle filter 2 via a supply line 14, which hot gas flow 18 comprises primarily ambient air which is inducted and pre-compressed to for example 1 bar or more by a compressor 16, which ambient air is heated to a desired temperature preferably directly by a burner 22 in a downstream combustion chamber 20, the desired temperature corresponding substantially to the exhaust-gas temperature of a simulated internal combustion engine during a predefined driving state. The desired temperature may lie for example in the range between 50° C. and 900° C. The compressor 16 may for example be a conventional rotary piston compressor, with it also being possible for two or more compressors to be connected together preferably in a cascaded fashion in order to increase the delivered air quantity or the admission pressure.

It may also be provided that the combustion chamber and the burner 22, whose temperature is preferably varied by means of the quantity of supplied fuel, can be bypassed by means of a bypass duct, which can be preferably electrically heated in order to also be able to simulate driving states at low rotational speeds of the internal combustion engine or else at idle of the latter at low ambient temperatures.

As is also shown in the FIGURE, a dosing device 24 is arranged below the particle storage container 8, which dosing device 24 receives the particles 10 from above via a passage (not shown in any more detail) at the lower end of the funnel-shaped filter housing 12. Here, the dosing device 24 comprises a feed worm 26 which is driven by means of an electric motor 28 and which supplies the particles 10 to a fluidization device 30 which comprises in particular a merely schematically illustrated venturi nozzle 32 which introduces the particles 10, which emerge from the feed worm 26, into a preferably inert carrier gas, in particular nitrogen, which is indicated in FIG. 1 by the arrow 34.

In the venturi nozzle 32, the particles 10 which are delivered by the feed worm 26 with a predefined delivery capacity, which is determined by means of the rotational speed of the electric motor 28, are delivered individually into the flow of carrier gas 34 which flows with an increased flow speed through the venturi nozzle 32, and are delivered by means of said flow of carrier gas 34 in fluid form along the supply line 36 to an injector 38 which introduces the particles 10 into the hot gas flow 18, by means of which said particles are then transported to the particle filter 2 in order to load the latter with a predefined quantity of particles 10, for example with a total of 20 g of particles.

The injector 38 preferably comprises a tube 40 which is inserted into the supply duct or the supply line 14 in the transverse direction, said tube 40 being directly flow-connected at its one end to the supply line 36 and being closed off at its other end, that is to say at its end side. A plurality of passage bores 42 are formed into the cylindrical-casing-shaped peripheral surface of the tube 40 on the downstream side, that is to say on the side facing toward the particle filter 2, through which passage bores 42 the fluid composed of particles 10 and inert carrier gas 34 emerges and is mixed with the hot gas flow 18 which is generated by the burner 22 and which is composed of heated air and exhaust gas from the burner.

As is also indicated merely schematically in the illustration of FIG. 1, the particle storage container 8 and preferably also the feed worm 26 are arranged on a weighing device or set of scales 44, which comprises a known set of electronic precision scales, by means of which the total weight of the particle storage container 8, which may be for example 80 or 100 kg, can be determined with an accuracy of, for example, plus/minus 1 g.

Here, in order to obtain additional mechanical decoupling of the particle storage container 8 from surrounding auxiliary units such as induction fans, inert gas generators and pumps, the weighing device 44 may be arranged on schematically shown vibration dampers 46. In this way, it is possible for the vibration-induced measurement inaccuracies of the weighing device 44 to be further reduced. Furthermore, the particle storage container 8 and the weighing device may be surrounded by a sound-absorbing hood (not shown in any more detail in FIG. 1) which further reduces the sound vibrations which are transmitted by ambient noises to the particle storage container 8 and from the latter to the weighing device 44, and also the influence of drafts and the like on the weighing result.

According to a further embodiment of the invention, a knocking and/or shaking device 50 may be arranged on the particle storage container 8, which knocking and/or shaking device 50 preferably periodically, for example every 5 seconds, sets the housing 6 of the particle storage container 8 in vibration or exerts one or more successive shocks to the housing 6 of the container 8 in order to break up accumulations or bridges of particles 10 which form as a result of the continuous extraction of the particles 10 at the base-side end of the container.

In the preferred embodiment of the invention, the weighing device 44 and preferably also the dosing device 24 are connected to an electronic control device 52 which, for example at time intervals of 2 seconds, compares the actual values, weighed by the weighing device 44, for the instantaneous total weight of the particle storage container 8 with a nominal value or default value, calculated in advance for the end of the time interval, for the instantaneous total weight, and correspondingly increases or reduces the delivery capacity of the dosing device 24 as a function of the result of said comparison. It is correspondingly also possible, instead of the nominal value for the instantaneous total weight of the container, to also take into consideration a value derived from said nominal value, in particular the total quantity of particles which has been extracted since the beginning of the measurement time period, which total quantity is calculated by the electronic control device 52 preferably continuously by calculating the difference between the initial total weight and the measured instantaneous total weight of the particle storage container 8.

For this purpose, the electronic control device 52 preferably increases the motor rotational speed, and therefore the delivery capacity of the feed worm 26, by a predefined and in particular manually variable fixed rotational speed default value, for example by 5% of the maximum rotational speed, if the actual value for the extracted total quantity of particles lies below the previously calculated nominal value for the measurement time. In a corresponding way, the motor rotational speed is lowered by the rotational speed default value if, at a determined measurement time, the actual value for the extracted total quantity of particles exceeds the associated nominal value.

Here, the electronic control device 52, which is preferably realized by means of a known electronic microprocessor circuit and associated software, calculates the actual value for the quantity of particles 10 which has been extracted since the beginning of the measurement time period by calculation as a running mean value from the last three or five measurements, as a result of which periodically repeating fluctuations of the actual value for the instantaneous total weight of the particle storage container 8, which fluctuations are caused in particular by the break-up of particle bridges by means of the knocking and shaking device 50, do not lead to an overshoot of the system during the adaptation of the delivery capacity of the dosing device 24.

The electronic control device 52 also preferably comprises an electronic memory 54 in which are stored the rotational speed default value and further process parameters, such as the time for the beginning and the end of a measurement and the default value for the total quantity of particles which has been extracted at the end of the measurement time period, etc.

Furthermore, the electronic control device 52 preferably also performs all the other measurement and display processes, such as the continuous measurement and display of the temperature within the particle filter 2 to be tested, the control and monitoring of the temperature of the burner 22, of the delivery capacity and the delivery pressure of the compressor 16, and of the delivery capacity of an inert gas generator (not shown in any more detail in the drawings) which may for example be a nitrogen generator which for example electrothermally separates the nitrogen directly from the ambient air, and also the actuation of the knocking and/or shaking device 50.

The invention claimed is:

1. A method for testing a particle filter for an internal combustion engine, the method which comprises:
    subjecting the filter, at an inlet side thereof, to a hot gas flow laden with particles;
    supplying the particles to the hot gas flow from a particle storage container by way of a dosing device; and
    determining a quantity of particles being introduced into the hot gas flow during a predefined measurement time period by weighing the particle storage container.

2. The method according to claim 1, which comprises supplying the particles as a fluid to the hot gas flow.

3. The method according to claim 2, wherein the fluid is an inert carrier gas or a gas containing an inert carrier gas.

4. The method according to claim 3, wherein the fluid is nitrogen or contains nitrogen.

5. The method according to claim 1, which comprises continuously determining a total quantity of particles that has been extracted from the particle storage container since a beginning of a measurement time period at predetermined time intervals by measuring an instantaneous total weight of the particle storage container as an actual value.

6. The method according to claim 5, which comprises varying a delivery capacity of the dosing device in dependence on the actual value for the extracted total quantity of particles.

7. The method according to claim 6, which comprises increasing the delivery capacity of the dosing device by a predefined value if the actual value for the extracted total quantity of particles lies below a nominal value, and reducing the delivery capacity of the dosing device by a predefined value if the actual value for the extracted total quantity of particles exceeds the nominal value.

8. The method according to claim 6, which comprises determining the actual value for the quantity of particles that has been extracted since the beginning of the measurement time period by calculation as a running mean value.

9. The method according to claim 6, which comprises determining the nominal value for the quantity of particles that has been extracted since the beginning of the measurement time period by calculation on the basis of the delivery capacity and the time duration which has elapsed since the beginning of the measurement time period.

10. The method according to claim 1, wherein the filter is a soot particle filter.

* * * * *